US005236333A

United States Patent [19]

Barba, Jr.

[11] Patent Number: 5,236,333

[45] Date of Patent: Aug. 17, 1993

[54] LEG EXERCISER

[76] Inventor: Alfonso Barba, Jr., 1103 Avenue X, Brooklyn, N.Y. 11235

[21] Appl. No.: 827,625

[22] Filed: Jan. 29, 1992

[51] Int. Cl.[5] .............................................. A61F 5/00

[52] U.S. Cl. .................................. 128/25 R; 482/125; 602/5

[58] Field of Search ......................... 602/5, 12, 23-26, 602/32, 35, 36; 128/25 R, 882; 482/131, 114, 124-125, 139, 900

[56] References Cited

U.S. PATENT DOCUMENTS

| | | | |
|---|---|---|---|
| 2,966,905 | 1/1961 | Kamenshine | 128/25 R |
| 3,000,632 | 9/1961 | Fuchs | 482/131 X |
| 4,407,496 | 10/1983 | Johnson | 482/139 X |
| 4,599,996 | 7/1986 | Seith et al. | 128/25 R |
| 4,606,542 | 8/1986 | Segal | 482/124 |
| 4,784,121 | 11/1988 | Brooks | 128/25 R |
| 4,801,138 | 1/1989 | Airy et al. | 128/25 R X |
| 4,844,454 | 7/1989 | Rogers | 128/25 R X |
| 5,020,797 | 6/1991 | Burns | 482/139 |
| 5,074,549 | 12/1991 | Harvey | 128/25 R X |
| 5,122,106 | 6/1992 | Atwood et al. | 128/25 R X |

*Primary Examiner*—Richard J. Apley
*Assistant Examiner*—Linda C. M. Dvorak

[57] ABSTRACT

The leg exerciser is a simple device, preferably made from bent tubing, with a foot support at one extremity of the tubing and a loose fitting knee engaging pad. The knee itself serves as a pivot for the exercising of a leg. The bent tubing forms as L shaped set of parallel rods, between which the foot may be engaged, supported between the rods. A knee pad is engaged on the rods over the knee. There is a handle at the end of the L shape of the rod. The handle can be used with great leverage for easily exercising the leg pivoting on the knee. The leg exerciser can alternately be engaged to a shoe from leg brace for the same use. The leg exerciser is simple to construct, inexpensive, and light weight.

27 Claims, 3 Drawing Sheets

LEG EXERCISER

FIELD OF INVENTION

This invention pertains to an exercise device for the exercise and rehabilitation of a leg.

BACKGROUND OF THE INVENTION

The present invention is a physiotherapy device for the exercise and rehabilitation of a leg. After a leg injury, or during a hospital stay, immobilized limbs tend to atrophy. After injuries, which may require immobilization, it is essential that the leg must be exercised in order to maintain its strength in order to rehabilitate. Weakened muscles in the leg oftentimes also need long term care.

While physiotherapy may be helpful in maintaining leg musculature and rehabilitating injured legs, it is oftentimes desirable to have a simple inexpensive device which will enable the individual to easily maintain self exercise.

Because of the nature of some disabilities of injuries, long term and readily available constant care are advisable. It is particularly desirable to have an ever available simple inexpensive device wherein a person themselves may be able to perform much of the necessary exercise or rehabilitation necessary to maintain or rehabilitate an injured leg.

It is important to have an effective, simple, easy to use, inexpensive device to effectuate exercise and rehabilitation of a leg.

DESCRIPTION OF THE RELATED ART

There are various complex systems and/or devices for exercise and/or maintenance of injured limbs.

U.S. Pat. No. 5,013,037 discloses a complex physical therapy device for the rehabilitation of the limb of a user. The device includes many straps to engage the device and hinging springs biased to pivot back and forth, adjacent the knee.

U.S. Pat. No. 4,892,302 is a cumbersome device, including a hinged leg support exerciser for stretching and strengthening leg muscles. The device may also vary the exercise stress by the use of dead weights.

U.S. Pat. No. 4,869,499 is exemplary of exercise devices for the leg and foot, attachable to a leg and a toe.

U.S. Pat. No. 2,467,943 is a complex spring bias exercising device for the leg with tension springs. The tension springs are engaged by a strap over the knee and with a foot support used to exercise the knee against the bias of the tension springs.

U.S. Pat. No. 2,198,995 is a traction device engagable with the upper leg and attachable to the lower leg.

U.S. Pat. No. 2,010,462 is a complex support mechanism attach to both legs with a sprocket chain system for pivoting the legs in a walking motion at the knees.

U.S. Pat. No. 2,887,033 is an artificial joint attachable above and below the knee, simulating actual joint action.

U.S. Pat. No. 2,384,779 is a fracture splint, employing longitudinal struts attached to the leg and supported against the upper leg, supporting the foot and maintaining the leg between the extended struts and a basic support for the splint.

U.S. Pat. No. 3,439,670 is a horse, knee and fetlock support, having a joint action as between the hoof portion and the leg portion of the support.

U.S. Pat. No. 4,573,940 is a body support and strut system from the waist to the feet for the support of a doll to maintain posture.

U.S. Pat. No. 4,669,450 is a complex, elongated rigid board secured to the back of the leg with straps and a leg board to hold the knee joint with an elongated handle for swinging the foot upward. The device is strapped to the leg.

U.S. Pat. No. 4,635,623 is a brace used, engaged above and below the knee for the limb to rotate through the same horizontal axis as the limb when the brace is applied.

U.S. Pat. No. 4,495,941 is a cast moving device, strappable to a plaster cast on the leg and including a handle on a string engaging the straps for the manipulation of a leg in a cast.

U.S. Pat. No. 2,146,842 is another splint engagable with the upper leg including rods engagable with a foot and a support for the support.

U.S. Pat. No. 3,000,632 is a complex exercising device designed to exercise a leg pivoting at the knee, the device being incorporated into a chair construction.

U.S. Pat. No. 4,784,121 is another similar device for exercising a bent knee extending from a seat, the device attachable to the seat and pivotable to raise and lower a leg by manipulation of a handle on a rod, pivoting from a pivot extending from a seat portion of the device.

U.S. Pat. No. 4,844,454 is a device, including a U shaped rod and leg support, strapped to the leg, where the leg can be exercised by tugging on the handle, pivoting the leg on the board from the underside of the knee.

SUMMARY OF THE INVENTION

The present invention is a simple device, preferably made from bent tubing, with a foot support at the extremity of the tubing and a loose fitting knee engaging pad to use the knee itself as a pivot for the exercising of a leg. The present invention combines strength and simplicity, the strength from the bent tubing, the simplicity from the structure forming an L shaped set of parallel rods, between which the foot may easily be engaged, supported between the rods. The knee pad then is engaged on the rods over the knee. The device then is firmly grabbed at the rod, forming a handle at the end of the L shape of the rod. It can be used with great leverage for easily exercising the leg. The device is easily engaged, easily disengaged and can be engaged from a sitting position or even engaged from a bed and then have the leg moved out of the bed for exercise.

An advantage of the device is that, for instance, it can be engaged while actually in bed and aid in having the user being able to swing the leg out over the edge of the bed for the purpose of exercise. Of course, the device is fully usable from a chair and in sitting position.

The device of the present invention is also adapted to exercise the knee when the foot is engaged in a conventional shoe for a leg brace.

According to the present invention a leg exerciser for exercising a person's lower limb in a rod configuration with a first portion. The first portion has a pair of rods extending substantially parallel. The first portion is of a length selected to extend substantially from along the thigh to the ankle. The first portion is wide enough to accommodate the leg and thigh. The first portion has a thigh end and an ankle end. There is a second portion at the thigh end of the first portion. The second portion is substantially perpendicular to the first portion and includes a handle and a support near the ankle end. The support is for the lower limb when the lower limb is engaged with the support. There is another support near the thigh end of the first portion to engage the knee from above. The handle is used to raise and lower the lower limb for exercise.

The rod configuration may be integral and may be L shaped and made from bent metal tubing. The rods of the first portion may be adjustable in length and may include telescopic end rods. The first portion and the end rods may have interactable stops for openings in both the rods of the first portion and end rods. A detent may interengage the rods. The detent may have a spring clip. The rods of the first portion may curve inward at the ankle portion.

The second portion may be U shaped and the handle may be integral to the second portion, The ankle end support means may be a band fixed between the end rods which may be slack to cradle a back portion of a foot.

The support band may be fixed to the end rods with a Velcro ® fabric set. The support band is preferably at end of the end rods. The thigh end support means may be a knee pad fixed straddling the rods. The knee pad may have an opening to receive the knee and may be slidably engaged on the rods. The knee pad may have straps with loops and adjustable belt loops over the rods and threaded through the loops.

There may be openings in the ends of each rod for a shoe having an engaged stirrup in the form of a U each arm of which has a detent. The detents engage in the rod opening to support the shoe in the end rods.

The support to support the person's lower limb may engage it from below when the lower limb is supported at the ankle end of the first portion.

Although such novel feature or features believed to be characteristic of the invention are pointed out in the claims, the invention and the manner in which it may be carried out, may be further understood by reference to the description following and the accompanying drawing.

BRIEF DESCRIPTION OF THE DRAWING

Referring now to the figures in greater detail, where like reference numbers denote like parts in the various figures.

DESCRIPTION OF THE PREFERRED EMBODIMENTS

Figure 1:
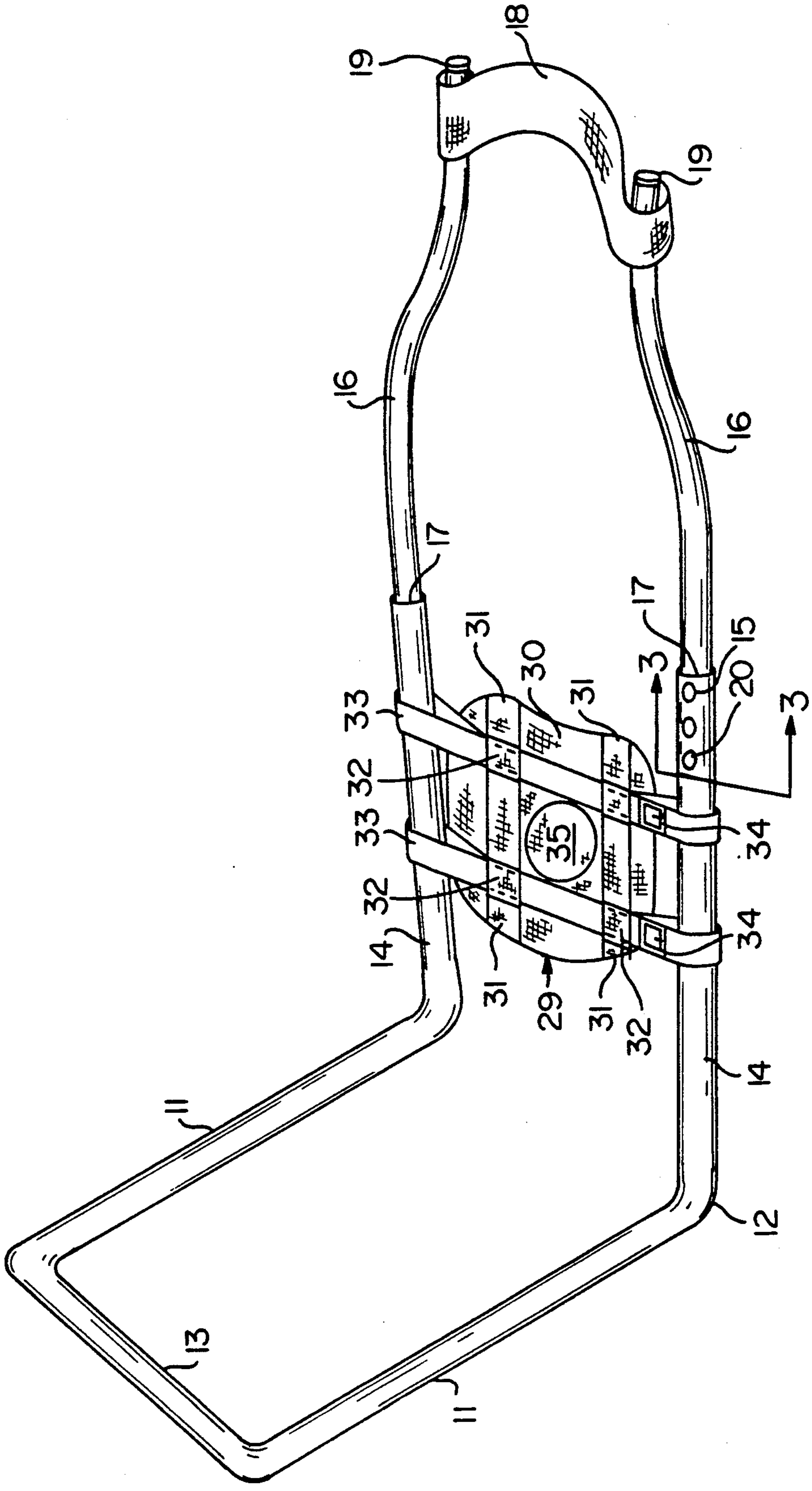
FIG. 1 is an isometric view of the leg exerciser of the present invention.
Figure 2:
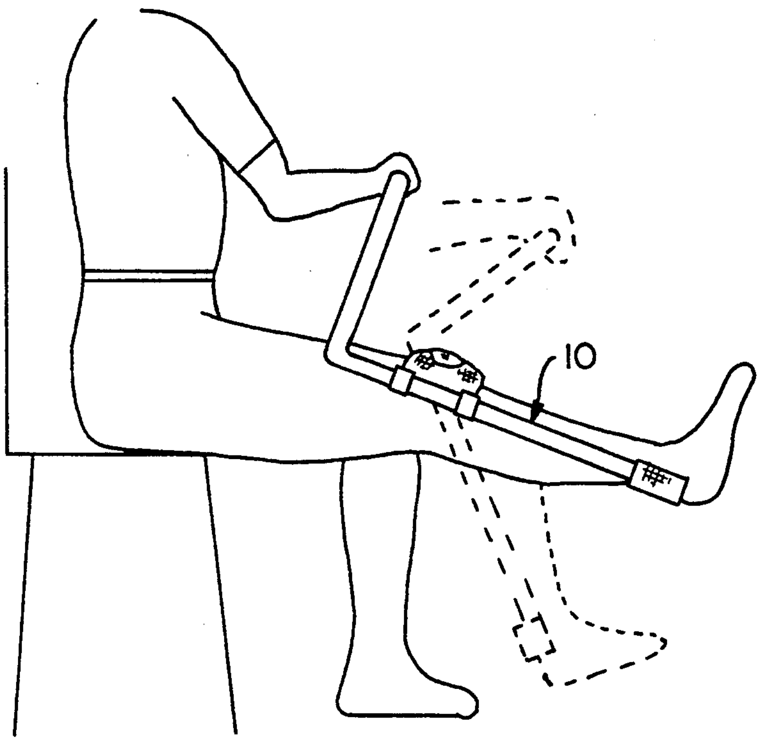
FIG. 2 is a schematic side elevation of the leg exerciser of the present invention in use.

The leg exerciser 10, as shown in FIGS. 1 and 2, comprises a first portion 11 made from bent metal tubing 12. The tubing 12 is bent into an integral unit including a handle portion 13, in the form of a U, extending rods 14, extending substantially at a 90 degree angle from the handle portion 13. The rods 14 are hollow and at their extreme ends, include spaced openings 15. End rods 16 are fitted into openings 17 in the extending rods 14. The extending rods 14 are substantially parallel to each other and are spaced away a distance, preferably wider than the normal leg and thigh.

The end rods 16 are bent away, off parallel, narrowing the gap between the end rods 16. The gap at the end of the end rods 16 is generally large enough to comfortably receive a foot and/or ankle in between. The end rods 16 are spanned by a support bend 18, affixed to the rod ends 19. The support band 18 forms a cradle for a foot or an ankle.

Figure 3:
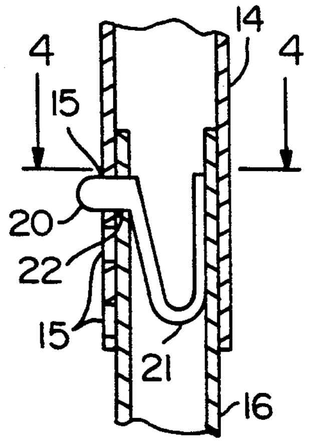
FIG. 3 is a section of FIG. 1 at lines 3—3.
Figure 4:
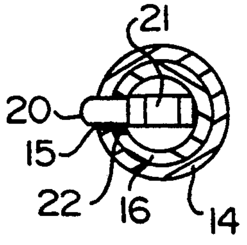
FIG. 4 is a section of FIG. 3 at lines 4-4.

The end rods 16 are adjustable as to length, engaged within the extending rods 14. As can be seen in FIG. 3, a detent 20 is biased by an integral spring 21 which passes through an opening 22 in the hollow end rod 16. As can be seen in FIG. 4, the detent 20 is also engaged through a selected opening 15 and locked into position. The section in FIG. 4 shows a detail section of FIG. 3 at lines 4—4.

Figure 5:
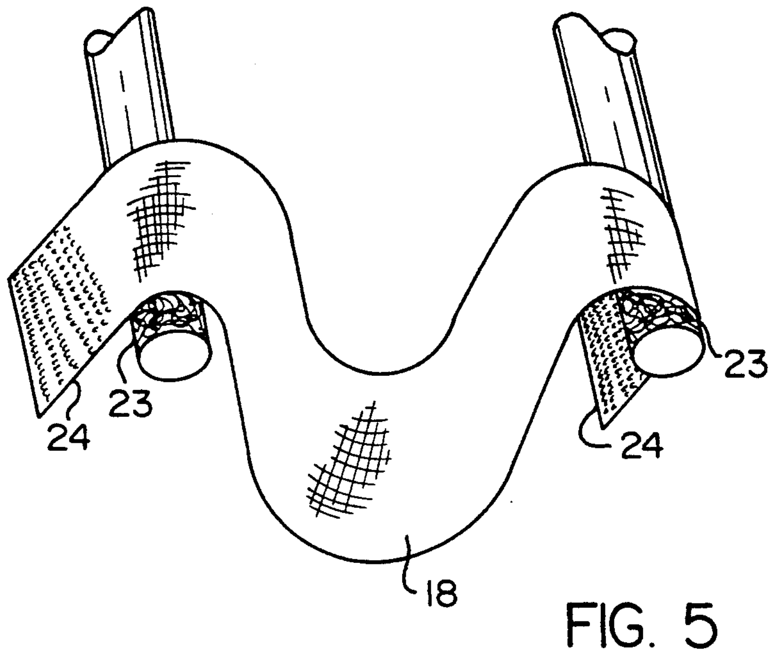
FIG. 5 is a detail of the end of the leg exerciser showing the support band unattached.
Figure 6:
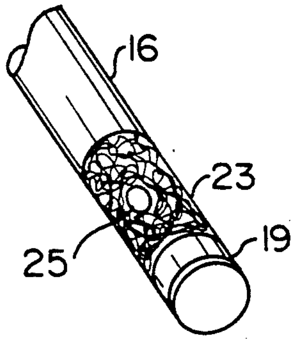
FIG. 6 is a detail of one rod end of the leg exerciser.

As shown in FIG. 5, the support band may be attached to the rod ends 19, with a Velcro ® two piece fabric set. As shown in FIGS. 5 and 6, the interengagable hook portion 23 is engaged around the rod ends 19, The interengagable hook portion 23 may be affixed by adhesives (not shown) or may come from a strip, including an adhesive backing. The ends of the support band 18 include a patch of an interengagable matted portion 24, which may be rolled around the rod end 19 to firmly hold the support band 18.

As can be seen in FIG. 6, the rod end 19, with its interengagable hook portion 23 includes an opening 25, passing through the rod end 19 and the interengagable hook portion 23. In another embodiment of the present invention, the rod ends 19 free of the support band 18, with the openings 25, can be engagable with a shoe 26. The shoe 26 is a conventional shoe with an integral U shaped stirrup 27. The shoe 26 with the stirrup 27 can be used with a conventional leg brace. The detents 28 on the stirrup 27 are engagable in the opening 25 of the rod ends 19, so that a shoe 26, from a brace, may be engaged in the openings 25 of the rod ends 19.

A knee pad 29 is straddled across the extending rods 14. In a preferred embodiment, the knee pad 29 comprises a knee engaging portion 30. The knee engaging portion 30 includes two sewn down straps 31. The straps 31 are formed into belt loops 32. Belts 33 are looped around the extending rods 14 and looped through the belt loops 32. The end of the loops 32 have buckles 34 to fasten the belts 33 from becoming disengaged. In a preferred embodiment, the knee engaging portion 30 includes an opening 35.

OPERATION

In use, the leg exerciser 10 is wide enough for a normal leg and thigh to be engaged between the two extending rods sets of the extending rods 14 and end rods 16.

The end rods 16 are selected for a length so that a large selection of individual leg and thigh lengths can be accommodated by a selected set of rods 14, 16. A selected number of openings 15 in the rods 14, accommodate the end rods 16, extending to the selected lengths.

The spring 21 is engaged at one end of the end rods 16. The spring 21 is biased to hold the spring 21 within the end rod 16. The detent 20 extends, biased outward, through an opening 22 in the end rod 16. The detent 20 extends a sufficient distance to pass through the end rods 16 and to engage itself in a selected opening 15 in an extending rod 14, as shown in FIGS. 3 and 4.

The detent 20 may be of a distinctly rounded configuration (not shown) so that it can be conveniently depressed to slide from one opening 15 to another, until the extending length of the end rod 16 has been selected.

The end rod 16, once engaged, preferably extending the same distance, form a structure substantially conforming to the leg with the rod ends 19 adjacent each other and prepared to receive the support band 18, as shown in FIG. 5 and 6. The rod ends 19 are covered with an interengagable hook portion 23 of fabric. The inner aspect of the support band 18 is covered by an interengagable matted portion 24 of fabric. The matted portions 24 are engaged around the interengagable hook portions 23 in a manner to loop the support band 18, so that it can cradle the heel and/or ankle, or leg portion.

The interengagable hook portion 23 and matted portion 24 are generally referred to as a Velcro ® set and may be attached to the rod ends 19 in an appropriate manner well known in the art.

The hook portions 23 and matter portions 24, of course, could be reversed for adequate attachment of the support band 18. Other means for the engagement of the support band 18 in its looped cradling configuration of the prior art, of course may be employed.

The knee pad 29 is preferably loosely engaged over the extending rods 14. The belts 33 are adjustable so that the knee pad 29 can have sufficient play to be comfortable in use and to also be able to slide back and forth so that the knee engaging portion 30 can be comfortably engaged with the knee in use. The straps 31 are sewn, or otherwise engaged, on top of the knee engaging portion 30, formed into the belt loops 32.

As a practical matter, the belts 33 are looped through the belt loops 32, so that both the belts 33 and straps 31 are on the upper surface of the knee engaging portion 30. This not only simplifies construction, but provides an under surface of the knee engaging portion 30, not likely to irritate the flesh of the knee. The opening 35 is further designed to accommodate the knee with a minimum amount of stress.

After the rods 16 have been selectively adjusted and the band 18 is attached, in used, either from a sitting position, or even in bed, the leg is extended through the spaced apart rod ends 16 with a foot and/or the ankle then resting upon the support band 18. The knee pad 29 is slid along the extending rods 14 until the knee engaging portion 30 is actually engaged with the knee. At that time, the handle portion 13 may be grasped to pivot the leg at the knee pad 29, to either lift the foot, or to raise the whole leg.

If the user is in bed, for instance, once the leg is engaged in the leg exerciser 10, by grasping the handle 13, the leg can be lifted and supported and swung out over the bed, so that the person using the leg exerciser 10 can be in a sitting position at a bed. The exercise, then, is performed by grasping the handle portion 13, pivoting the leg upward by pulling backward, using the knee pad 29 as the fulcrum of a lever. The leg can then be lifted and lowered and be engaged in various selected exercises or physiotherapy.

The simplicity of the leg exerciser 10 and the ease of being able to engage the leg, permits the device to be simply constructed, relatively inexpensive to manufacture and is adaptable to different exercise or physiotherapeutic techniques.

Figure 7:
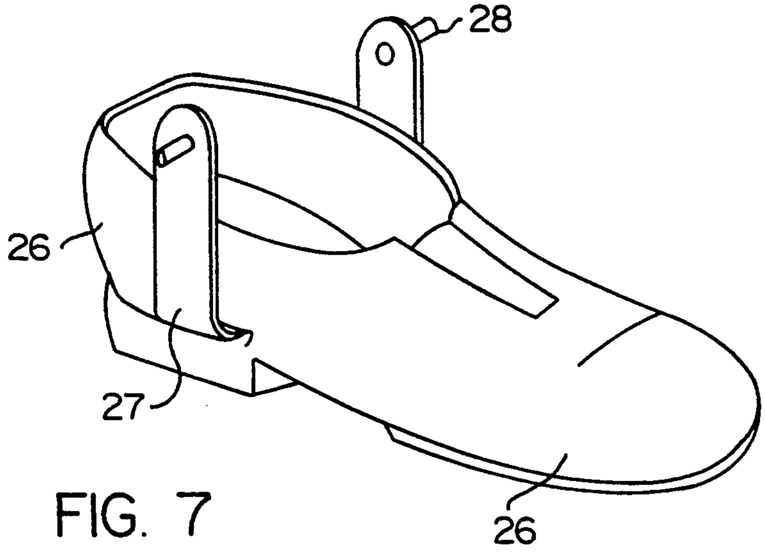
FIG. 7 si a view from a leg brace employable with the leg exerciser of the present invention.

Oftentimes, a person having a limb, which requires exercise or therapy, may also have a leg brace, including an integral shoe. A shown in FIGS. 6 and 7, a conventional leg brace shoe 26, usable with a leg brace (not shown) includes an integral stirrup 27 with detents 28 engagable with the conventional leg brace.

In another embodiment of the present invention, the rod end 19 of the end rod 16, is provided with an opening 25, as can be seen in FIG. 6. The opening 25 may pass through the interengagable hook portion 23 on the rod 19.

With the strap 18 removed, the openings 25 in the end rods 16, may be engaged with the detents 28 on the stirrup 27 of the shoe 26 and the exerciser 10 engaged for use as heretofore set forth.

The leg exercise 10 is preferably made of bent metal tubing 12. Hollow bent metal tubing is inexpensive, light weight and structurally strong. The first portion 11 conveniently extends the handle portion 13 to a point where it can be easily grasped by the user. The U shaped configuration of the first portion 11 and handle 13 allows the handle 13 to be pulled substantially backward and over the thigh, while the entire leg exerciser pivots from the knee engaged with the knee pad 29, as can be seen in FIG. 2.

The terms and expression which are employed are used as terms of description; it is recognized, though, that various modifications are possible.

It is also understood the following claims are intended to cover all of the generic and specific features of the invention herein described, and all statements of the scope of the invention which, as a matter of language, might fall therebetween.

What is claimed is:

1. A leg exerciser for exercising a person's lower limb comprising a rod configuration having a first portion, said first portion comprising a pair of rods extending substantially parallel, said first portion of a size selected to have a length extending substantially from a point along the person's thigh to a point near the person's ankle, said first portion having space between said rods along its length to accommodate the width of the person's leg and thigh therebetween, said first portion having a thigh end, said first portion having an ankle end, a second portion, said second portion at said thigh end of said first portion, said second portion substantially perpendicular to said first portion, said second portion including a handle, support means near said ankle end of said first portion, said support means to support the person's lower limb when said lower limb is engaged with said support means at said ankle end of said first portion, and a support means at least near said thigh end of said first portion, said support at said thigh end including a knee pad, said knee pad adapted to overlay the top of the user's knee, wherein said knee pad engages the person's knee when said handle is operated thereby raising and lowering the person's lower limb.

2. The invention of claim 1 wherein said rod configuration is integral.

3. The invention of claim 1 wherein said said rod configuration is L shaped.

4. The invention of claim 1 wherein said rod configuration is made from bent metal tubing.

5. The invention of claim 1 wherein said rods of said first portion are adjustable in length.

6. The invention of claim 5 wherein said rods of said first portion include end rods.

7. The invention of claim 6 wherein said end rods are telescopic.

8. The invention of claim 6 wherein said rods of said first portion and said end rods include interactable stop means.

9. The invention of claim 8 wherein interactable stop means include at least one opening in said rods of said first portion and at least one opening in said end rods.

10. The invention of claim 9 including detent means to interengage said rods of said first portion and said end rods.

11. The invention of claim 10 wherein said detent means include a spring clip.

12. The invention of claim 1 wherein said rods of said first portion curve inward at said ankle portion to cradle the user's ankle.

13. The invention of claim 1 wherein said second portion is U shaped.

14. The invention of claim 13 wherein said handle is integral to said second portion.

15. The invention of claim 6 wherein said ankle end support means is a band affixed between said end rods.

16. The invention of claim 15 wherein said band is slack.

17. The invention of claim 16 wherein said slack in said band is to cradle a back portion of a foot.

18. The invention of claim 15 wherein said support band is affixed to said end rods by means of an interengagable hook and matted portion set, one part affixed at each end of said support band and one part affixed to said end rods.

19. The invention of claim 15 wherein said ankle end support means is a band affixed between said end rods at the end of said end rod.

20. The invention of claim 6 wherein said thigh end support means is a knee pad.

21. The invention of claim 20 wherein said knee pad is affixed straddling said pair of rods.

22. The invention of claim 20 wherein said knee pad is slidably engaged on said pair of rods.

23. The invention of claim 22 wherein said knee pad includes straps with loops and adjustable belts looped over said rods and threaded through said loops.

24. The invention of claim 1 wherein said ankle end support means includes an opening in the end of each end rod at said ankle end.

25. The invention of claim 24 in combination with a shoe, said shoe including an engaged stirrup, said stirrup in the form of a U, each arm of said U including a detent, said detents to engage in said rod opening to support said shoe in said end rods.

26. The invention of claim 1 wherein said support means to support said person's lower limb engages said lower limb from below at when said lower limb is engaged with said ankle end of said first portion.

27. A leg exerciser for exercising a person's lower limb comprising a rod configuration having a first portion, said first portion comprising a pair of rods extending substantially parallel, said first portion of a size selected to have a length extending substantially from a point along the person's thigh to a point near the person's ankle, said first portion having space between said rods along its length to accommodate the width of the person's leg and thigh therebetween, said first portion having a thigh end, said first portion having an ankle end, a second portion said second portion at said thigh end of said first portion, said second portion substantially perpendicular to said first portion, said second portion including a handle, support means near said ankle end of said first portion, said support means to support the person's lower limb when said lower limb is engaged with said support means at said ankle end of said first portion, and a support means at least near said thigh end of said first portion, said support at said thigh end including a knee pad having an opening therein to receive the knee, said knee pad adapted to overlay the top of the user's knee, wherein said knee pad with said opening therein engages the person's knee when said handle is operated to raise and lower the person's lower limb.

* * * * *